(12) United States Patent
Grudin

(10) Patent No.: US 11,890,089 B1
(45) Date of Patent: Feb. 6, 2024

(54) FLOWMETER FOR AIRWAY RESISTANCE MEASUREMENTS

(71) Applicant: Oleg Grudin, Montreal (CA)

(72) Inventor: Oleg Grudin, Montreal (CA)

(73) Assignee: THORASYS THORACIC MEDICAL SYSTEMS INC., Montréal (CA)

( * ) Notice: Subject to any disclaimer, the term of this patent is extended or adjusted under 35 U.S.C. 154(b) by 1175 days.

(21) Appl. No.: 16/400,578

(22) Filed: May 1, 2019

Related U.S. Application Data

(63) Continuation-in-part of application No. 15/222,396, filed on Jul. 28, 2016, now abandoned.

(60) Provisional application No. 62/197,624, filed on Jul. 28, 2015.

(51) Int. Cl.
| A61B 5/085 | (2006.01) |
| A61B 5/087 | (2006.01) |
| G01F 1/684 | (2006.01) |
| G01N 25/20 | (2006.01) |
| A61B 5/097 | (2006.01) |

(52) U.S. Cl.
CPC ............ *A61B 5/085* (2013.01); *A61B 5/0878* (2013.01); *A61B 5/097* (2013.01); *G01F 1/684* (2013.01); *G01N 25/20* (2013.01); *A61B 2562/0247* (2013.01); *G01N 2333/435* (2013.01)

(58) Field of Classification Search
None
See application file for complete search history.

(56) References Cited

U.S. PATENT DOCUMENTS

| 4,403,514 | A | * | 9/1983 | Osborn ............... A61B 5/0876 600/538 |
| 4,989,456 | A | * | 2/1991 | Stupecky ............. A61B 5/0876 73/863.53 |
| 5,233,998 | A | | 4/1993 | Chowienczyk |
| 5,634,471 | A | | 6/1997 | Fairfax et al. |
| 5,763,792 | A | | 6/1998 | Kullik |
| 5,868,681 | A | | 2/1999 | Schiller |
| 6,066,101 | A | | 5/2000 | Johnson et al. |
| 6,149,603 | A | * | 11/2000 | Parker ............... A61M 16/0488 128/207.14 |
| 6,631,716 | B1 | | 10/2003 | Robinson et al. |
| 6,718,975 | B2 | | 4/2004 | Blomberg |
| 2002/0162397 | A1 | | 11/2002 | Orr |
| 2003/0140925 | A1 | | 7/2003 | Sapienza et al. |
| 2003/0183437 | A1 | | 10/2003 | Mendoza |
| 2009/0250059 | A1 | | 10/2009 | Allum et al. |
| 2010/0071693 | A1 | | 3/2010 | Allum et al. |
| 2012/0004571 | A1 | | 1/2012 | Ku |
| 2012/0085347 | A1 | | 4/2012 | Iyer et al. |

(Continued)

FOREIGN PATENT DOCUMENTS

| WO | 01/18496 A2 | 3/2001 |
| WO | 2013/098714 A1 | 7/2013 |

(Continued)

OTHER PUBLICATIONS

U.S. Appl. No. 15/222,396 office action dated Jan. 11, 2018.

*Primary Examiner* — Jacqueline Cheng
*Assistant Examiner* — Jairo H Portillo

(57) ABSTRACT

A flowmeter has a disposable flow tube and a part of the shutter which are in direct contact with exhaled air and protect the rest of the device from potential contamination with harmful viruses.

8 Claims, 7 Drawing Sheets

(56) References Cited

U.S. PATENT DOCUMENTS

2014/0276173 A1  9/2014  Banner et al.
2016/0106341 A1  4/2016  Adam et al.

FOREIGN PATENT DOCUMENTS

WO    WO 2015/005958 A1    1/2015
WO    WO 2015/066812 A1    5/2015

* cited by examiner

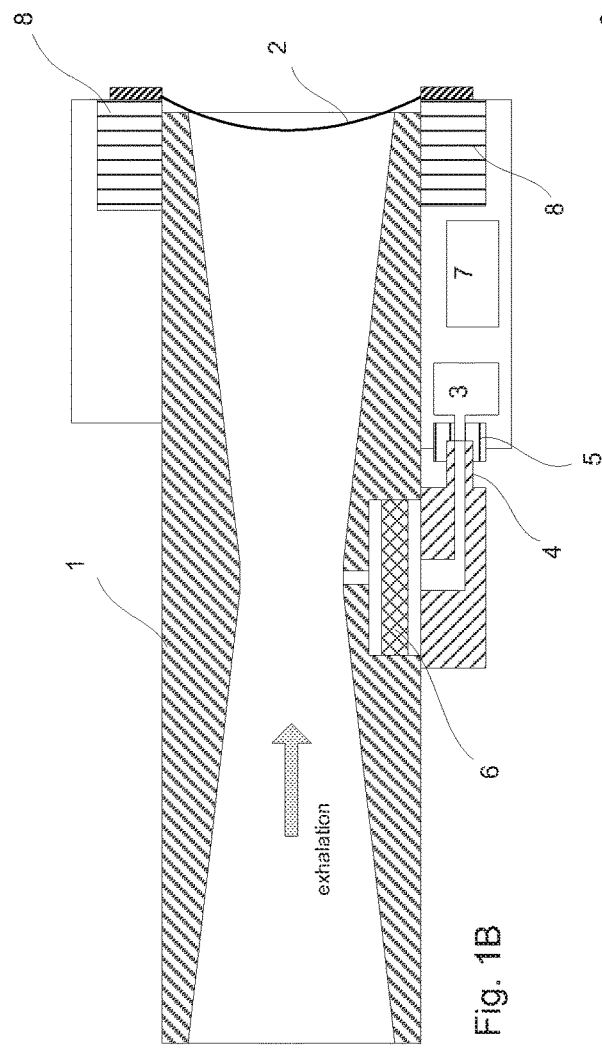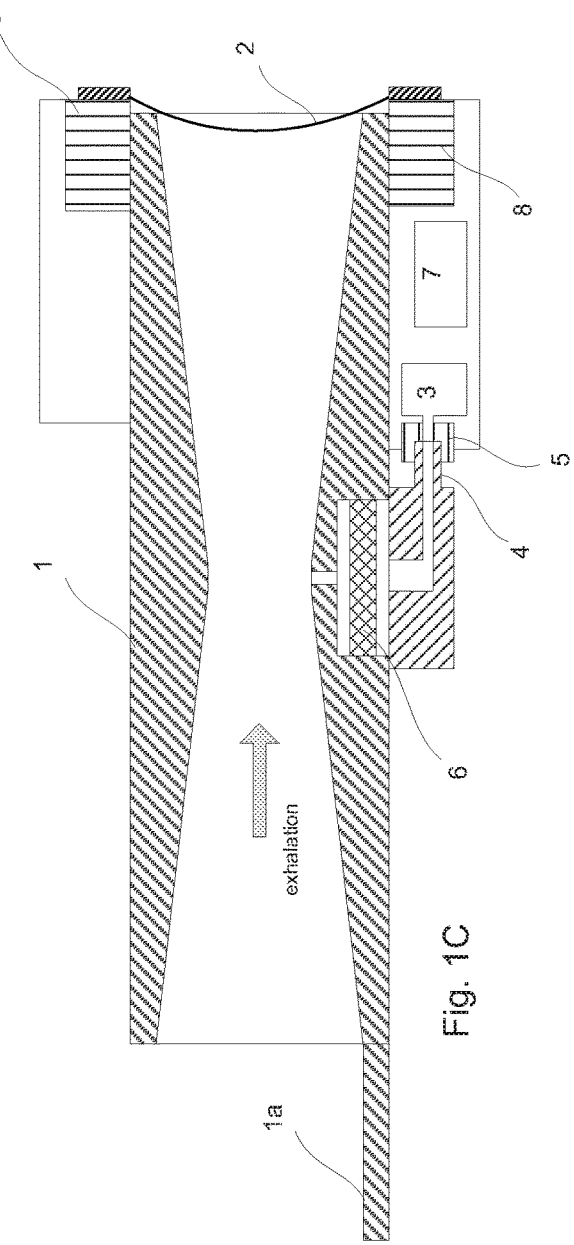

FLOWMETER FOR AIRWAY RESISTANCE MEASUREMENTS

This application is a continuation of U.S. patent application Ser. No. 15/222,396 filed on Jul. 28, 2016 that claims priority of U.S. provisional patent application 62/197,624 filed Jul. 28, 2015, the specification of which is hereby incorporated by reference.

The present application relates to medical diagnostics devices, more particularly to devices that measure respiratory parameters such as airway resistance.

One known method and the device for measuring airway resistance are known from Applicant's PCT/CA2014/051073 filed on 6 Nov. 2014 and published as WO2015/066812 on 14 May 2015. According to this reference, the subject exhales quietly into the flowmeter with distal end initially closed by the shutter. During the occlusion stage, pressure inside closed flowmeter increases. After pressure exceeds predetermined pressure, the shutter is opened, and the device measures the post-occlusion air flow spike. Airway resistance is calculated based on data on occlusion pressure and air flow waveforms.

The device described in the earlier patent application can operate with one gauge sensor which measures positive pressure with respect to ambient during occlusion and negative pressure with respect to ambient caused by air flow after the shutter release. Due to Bernoulli's effect, drop in pressure (negative pressure relative to ambient) caused by increased air velocity through restriction in the flow tube pulls in (entrains) air through the port. This entrainment effect can be created for example in Venturi or Pitot tube. Traditional calibration process determines relation between negative pressure and air flow through the tube.

DESCRIPTION OF THE PREFERRED EMBODIMENTS

One object of the proposed solutions is to propose a design of the flowmeter with a disposable flow tube and part of the shutter which are in direct contact with exhaled air and protect the rest of the device from potential contamination with harmful viruses.

Another object of some embodiments is to improve performance of the flowmeter by increasing of pressure response versus flow and simplifying linearization of the device.

BRIEF DESCRIPTION OF THE DRAWINGS

In the drawings:

FIG. 1B is a schematic view of the assembled device for airway resistance measurements showing a reusable electro-mechanical module, a disposable flow tube and a shutter lid occluding a distal end of the flow tube;

FIG. 1C is a schematic view of a variant device for airway resistance measurements showing a tongue depressor integrated into a proximal end of the disposable flow tube;

DETAILED DESCRIPTION

Disposable Flow Tube

Figure 1A:
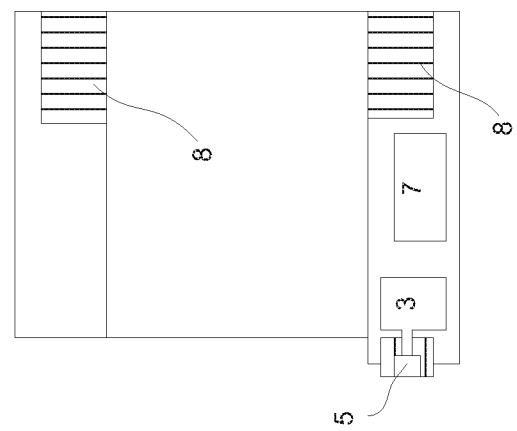
FIG. 1A is a schematic view of the device for airway resistance measurements disassembled showing a reusable electro-mechanical module, a disposable flow tube and a shutter lid which can occlude a distal end of the flow tube.
Figure 1A:
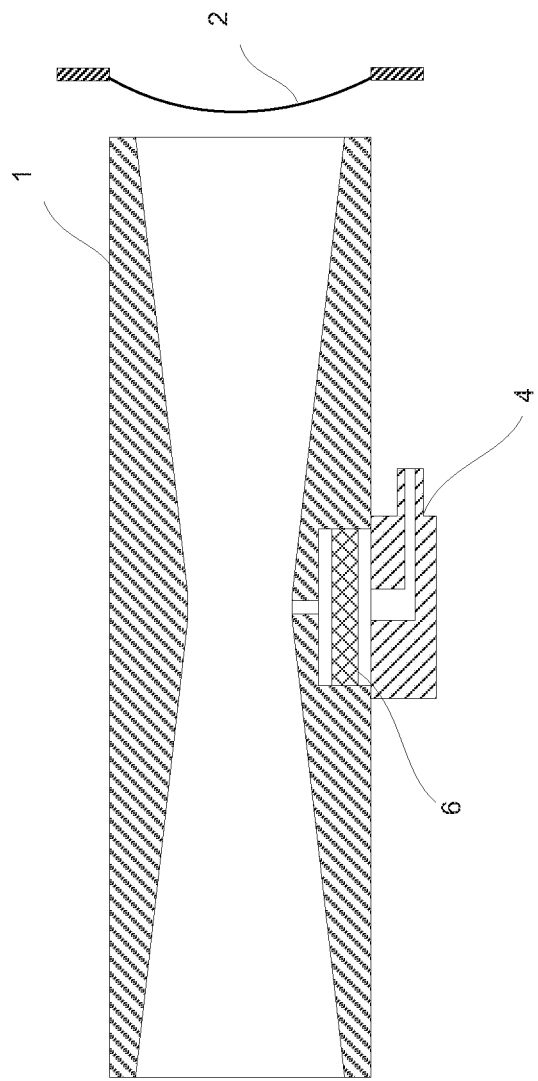
Figure 2A:
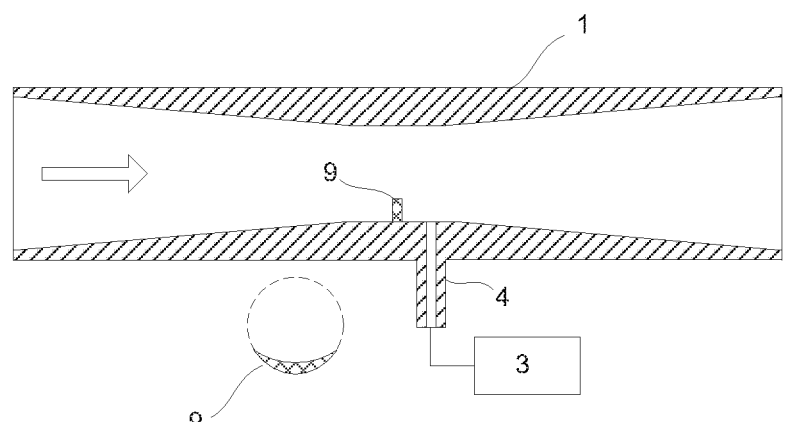
FIG. 2A presents a schematic view of a disposable flow tube with a baffle and its connection to one pressure sensor.
Figure 2B:
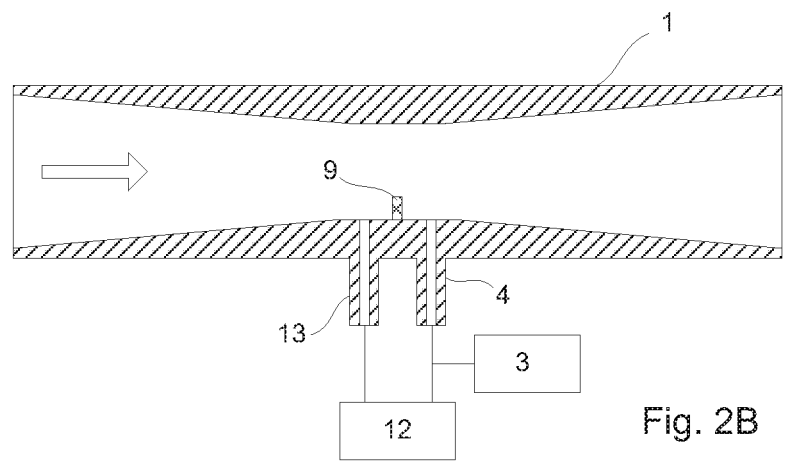
FIG. 2B presents a schematic view of a disposable flow tube with a baffle and its connection to two pressure sensors.
Figure 3:
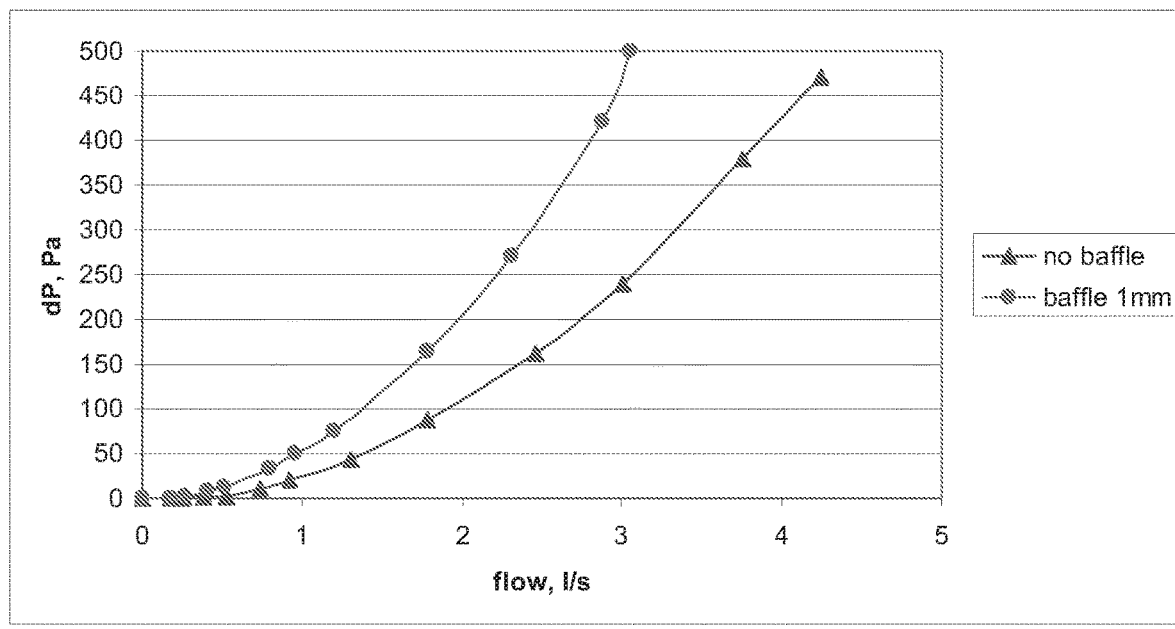
FIG. 3 shows pressure from flow response of the flow tube.
Figure 4:
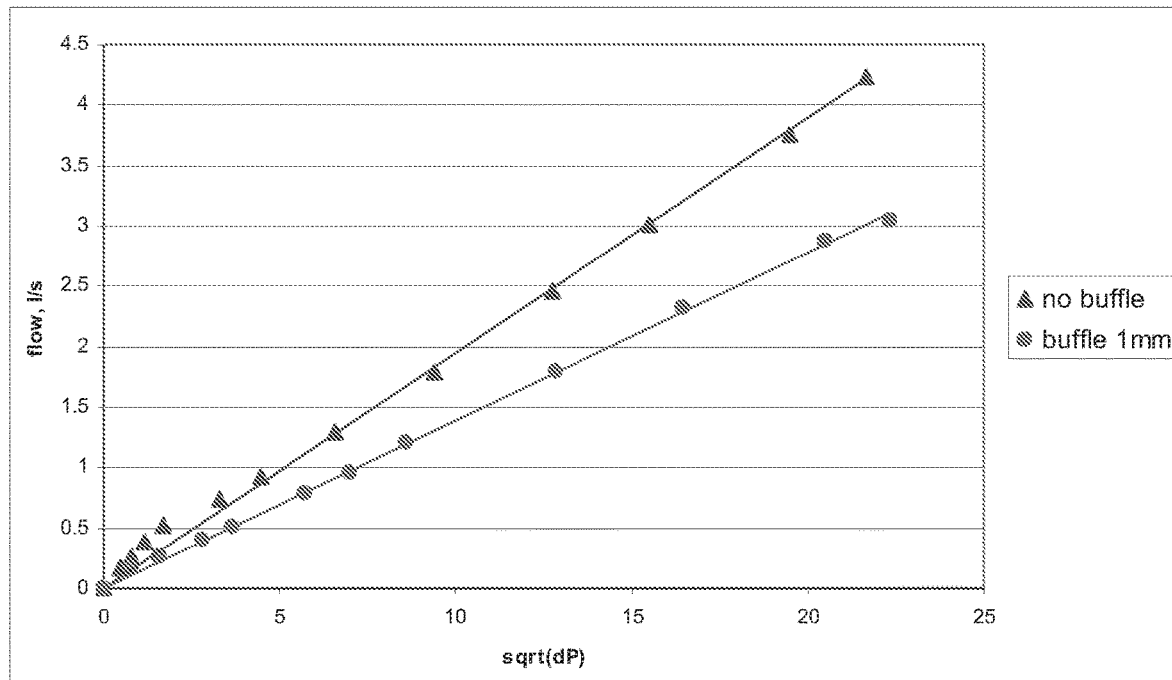
FIG. 4 shows calibration curves of the flow tube presented as flow versus square root of pressure.
Figure 5:
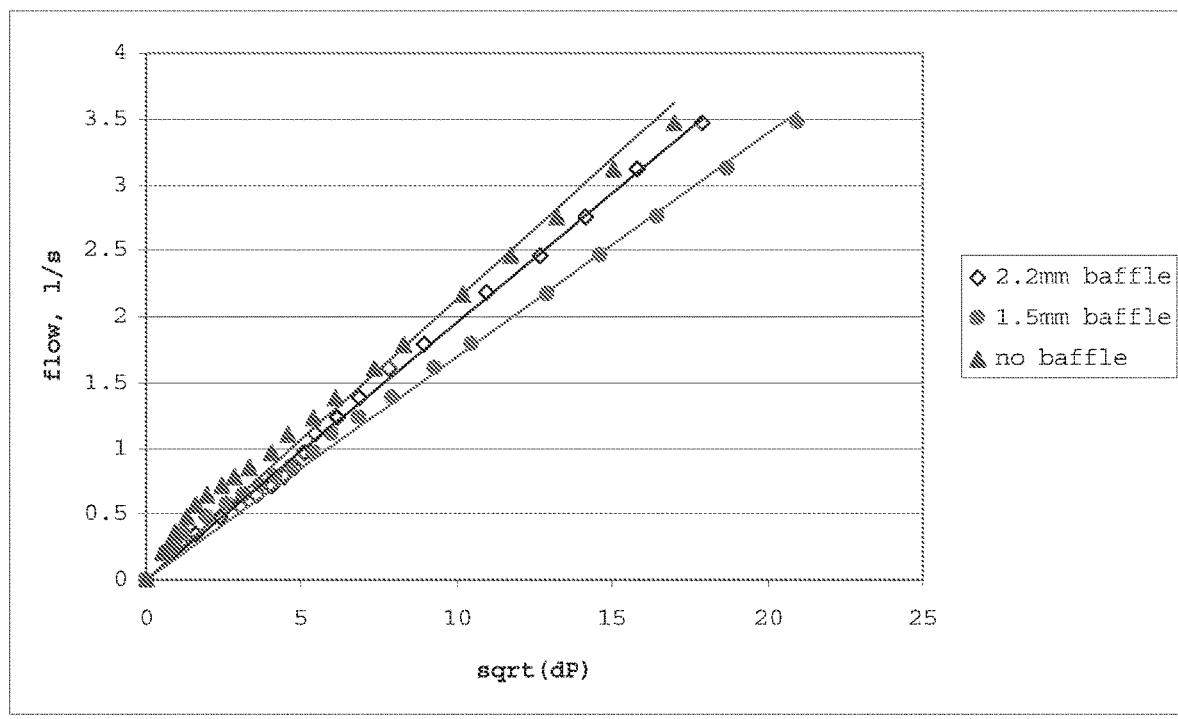
FIG. 5 shows calibration curves of the flow tube with different baffles.
Figure 6:
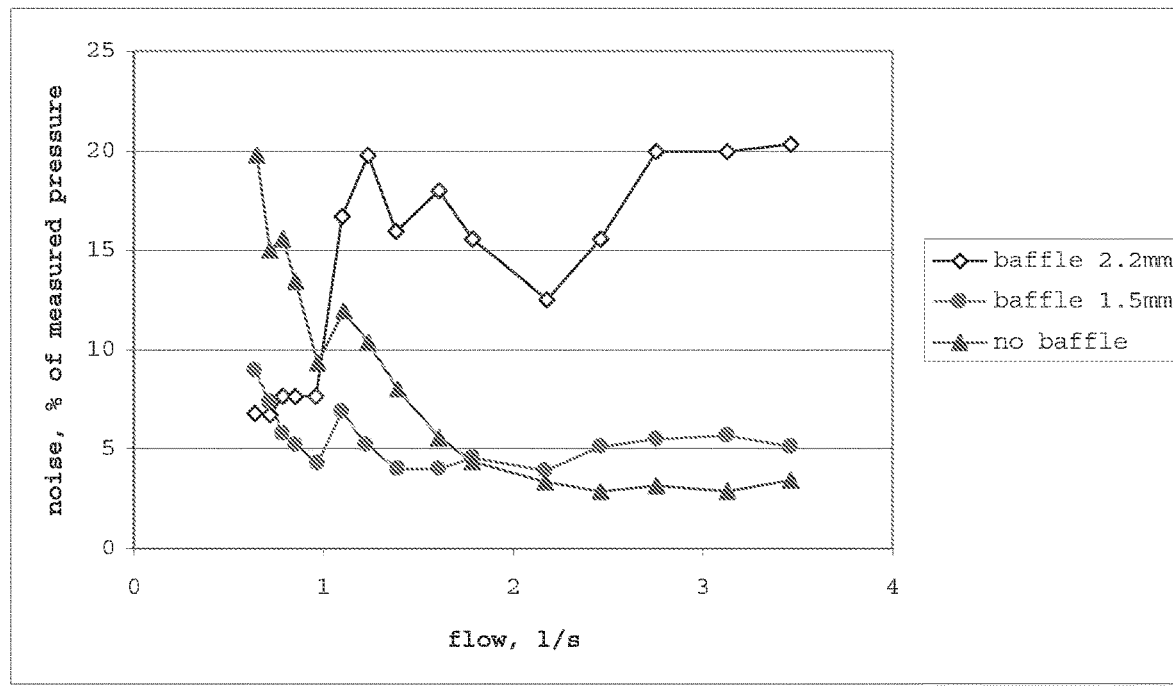
FIG. 6 shows pressure noise measured for the flow tube with different baffles.

One of possible embodiments of the respiratory device is illustrated in FIG. 1A and FIG. 1B. The device consists of disposable flow tube 1, the shutter or cap 2 of the shutter and permanent electro-mechanical module.

The seal between the flow tube 1 and the shutter 2 can be improved by providing a gasket. The shutter 2 and/or the permanent electro-mechanical module can have a holder or support for the disposable shutter, such as a frame or hinge mechanism to support the disposable part while operating as shutter. In the embodiment illustrated in FIG. 1B, the shutter 2 has a plastic spherical middle surface with a ferromagnetic rim ring that is all disposable.

During the measurements, the flow tube 1 is attached to the electro-mechanical module such that gauge pressure sensor 3 is in pneumatic connection with the flow tube. Pneumatic port 4 of the tube is connected to the input of the sensor 3 through the adaptor 5.

To avoid propagation of the viruses which may be present in air flow, filter 6 is attached to the flow tube 1 between inner surface of the tube and pneumatic port 4.

Because the flow rate through the sensor 3 is small in this configuration, the filter can pose relatively high resistance without adversely affecting flow or pressure measurements using the sensor 3.

With such configuration of the device, electro-mechanical module which may include also micro-controller 7 and shutter mechanism 8 is isolated from exhaled air and protected from contamination.

In the embodiment of FIGS. 1A and 1B, the flow tube 1 can be provided sterile to the patient for single use, while the electro-mechanical module can be reused.

The micro-controller 7 can alternatively comprise a data interface, for example a Bluetooth wireless link, so that signal collection and/or processing can be performed using a separate unit such as a smartphone, tablet or personal computer. This allows for the user interface to be external to the reusable module. The permanent electro-mechanical module can have a battery that can be rechargeable.

It will be appreciated that the reusable module can include an independent user interface, such as an audio signal and/or signal lights and/or a small display, for interacting with the user during trials. The final measurement can be communicated to the user in a variety of ways. In some cases, only a comparative measurement is required, so the result can be communicated with a very simple indicator (visual or audio). Text to speech can also be used to communicate a measurement in audio form instead of a visual display. Result data can also be communicated by a data link, while patient interaction is done using indicators (audio or visual) on the device itself.

While the shutter release mechanism 8 shown is a magnetic release mechanism, a user actuated mechanical trigger can be provided. If desired, the micro-controller can signal to an audio transducer an audio signal to prompt the user to use the trigger mechanism.

The shutter control is illustrated as an electro-magnetic release, however, a mechanical release mechanism using a piezo-electric actuator, electric motor, solenoid, etc. can also be contemplated. A manual release can also be used, although with greater need for operator cooperation and thus a risk for measurement error.

In the embodiment of FIGS. 1A and 1B, the filter is provided before port 4 in the body of the tube 1. Alternatively, the filter 6 can be provided at the port 4, with the coupling of the port being possibly larger to accommodate the filter 6.

In the embodiment of FIGS. 1A and 1B, sensor 3 is a part of the reusable module, and the filter 6 acts to protect the sensor from contamination. Two variants to filter 6 are contemplated.

One variant is to measure the volume of air that is able to be drawn from sensor 3 into tube 1 during the largest exhalation expected. Then the volume of the passage from sensor 3 to the tube 1 can be arranged to be bigger than what the one or more exhalation trials could transport back from sensor 3 any possible virus or microbe. A labyrinth passage between tube 1 and port 4 could be provided. This would replace the need for the filter 6.

Following quantitative example demonstrates possibility to build such labyrinth. Assume that pressure in the flow tube during occlusion monotonically increases from zero to 1000 Pa in 1 second. Calorimetric type thermal sensor with pneumatic impedance of 50 kPa*s/ml is used to measure said pressure. Volume of air leaking through the sensor during occlusion is about 0.01 ml. If the capillary with cross section of 2×2 mm is built around the flow tube with outer diameter of 2 cm, its volume is 0.25 ml. Even one loop of such capillary having volume 25 times bigger than the volume leaking from the flow tube during occlusion can protect the sensor from contamination. Note that during post-occlusion cycle, air flows in opposite direction—from the sensor into the flow tube.

A second variant is to arrange the sensor 3 in the disposable tube 1 and to provide an electrical connection between the reusable module and the disposable tube 1. In this case, the filter 6 is not required. This variant is not optimal because the sensor 3 also must keep information on its individual calibration. Therefore memory circuitry would still be needed and the reusable module would also need to read the memory to retrieve the calibration data (or otherwise the processor 7 would need to obtain the calibration data), or the sensor 3 would still need to have a processor to calibrate its signal so that the flow data was adjusted by the calibration data. This can increase the cost of the disposable tube 1.

In the embodiment of FIG. 1C, the proximal end of the tube 1 has a tongue-depressor extension 1*a* that can be positioned to rest on the user's tongue so that the tongue does not close part of the flow tube opening altering air flow measurements and thus airway resistance measurement results.

Baffle for Improved Flow Measurement Response

FIG. 2*a* shows experimental Venturi-type flow tube 1 with one pneumatic port 4 connected to the gauge sensor 3. The tube was tested without bacteriological filter. One tube tested had a length of 80 mm with an input diameter of 15.5 mm and diameter in the narrowest part of 13 mm. It will be appreciated that variations in dimensions and shape are possible.

The flow tube was characterized without baffle and with baffle 9 having height of 1 mm. FIG. 3 shows experimentally measured pressure response in both cases. Generated pressure (negative with respect to ambient) for the flow tube with baffle exceeds pressure for no-baffle tube by factor of ~2 for medium flows and ~5 for low flows.

The arrangement of a baffle in a flow tube is known per se from PCT patent publication WO01/18496 A2 published 15 Mar. 2001 (see for example FIG. 8A).

In both cases of baffle and no baffle, the generated pressure is close to the square function of flow. FIG. 4 shows calibration curves of both tubes presented with axes "flow" and "square root of pressure". Note that in real operation, flow through the flowmeter is restored from pressure (measured by gauge sensor 3). Pressure response of the flow tube with baffle provides more accurate flow measurement and requires simpler linearization procedure because flow is almost linear function of "square root of pressure". Alternatively, the flow tube without baffle requires more complicated linearization due to essential deviation of calibration curve from linear function of "square root of pressure" at low flows.

It was experimentally found that there is optimal value of the baffle height for the tube with certain geometry. FIG. 5 shows calibration curves of the second tube with a length of 82 mm, input diameter of 19 mm and diameter in the narrowest part of 14 mm. The tube without baffle has the lowest sensitivity and essential deviation from pure "square root of pressure" function at low flows. Sensitivity here is treated as ability of the tube to generate entrainment pressure as function of flow. Sensitivity of the tube with the baffle of intermediate height of 1.5 mm is higher than for the no-baffle tube but also higher than for the tube with bigger baffle with 2.2 mm height.

Additional advantage of the baffle with intermediate height is that pressure noise caused by flow turbulence is lower than for the bigger baffle. FIG. 6 shows noise measured as percentage of measured entrainment pressure. Noise for the tube with 2.2 mm baffle is about four times bigger than for the tube with optimal (1.5 mm) baffle.

It is assumed that for the flow tube of Venturi type generating entrainment pressure, baffle with optimal geometry (height) must be found. Tube design optimization may include experimental characterisation of the tubes with different baffles and experimental selection of the baffle design which provides the highest sensitivity with optimal pressure noise. Alternatively theoretical simulation of the flow tube can be done to determine optimal design.

FIG. 2*b* shows another embodiment of the Venturi-type flow tube 1 with baffle 9. This tube contains additional pneumatic port 13 with differential pressure sensor 12 connected to the ports 4 and 13.

Gauge sensor 3 operates as was described above and measures pressure during occlusion stage and post-occlusion flow spike. Data from the sensor 3 are used for calculation of airway resistance. Sensor 12 can be used to determine direction of flow through the tube 1. With this flowmeter, it is possible to provide multiple airway resistance measurements during spontaneous breathing. After occlusion stage and post-occlusion flow spike, the subject continues spontaneous breathing through the flow tube. Sensor 12 together with sensor 3 can determine end of inspiration and generate signal for shutter closing. Airway resistance measurements can be repeated automatically multiple times at the beginning of exhalation.

The flow tube with baffle having optimized sensitivity and noise can be made in a non-disposable form in accordance with an embodiment similar to FIG. 1.

It should be noted that additional technical solutions may be used by those skilled in the art to improve and extend some features of the device. For example the flow tube can be attached to specially designed mouthpiece to provide optimal and comfortable usage by the subject. Alternatively the proximal end of the flow tube can be specially shaped to better fit mouth of the subject.

What is claimed is:

1. A device for measuring airway resistance comprising:
a shutter;
a flow tube having a proximal end, for engaging a patient's mouth, a distal end, for receiving said shutter to releasably occlude said flow tube, and a medial pneumatic port;
a baffle located upstream of said pneumatic port, said baffle projecting from a sidewall near said pneumatic port so as to create a negative pressure at said pneumatic port;
a sensor for measuring pressure in said flow tube during occlusion and entrainment pressure caused by air flow through the tube during exhalation, wherein said sensor is in communication with said pneumatic port; and
a shutter release mechanism to keep said flow tube closed with said shutter during occlusion and to release said shutter at the end of occlusion.

2. The device as defined in claim 1 wherein said sensor is a calorimetric thermal flow sensor having two ports, a first port being in communication with said medial pneumatic port and a second port being in communication with ambient air.

3. The device as defined in claim 1, further comprising a bacteriological filter between said medial pneumatic port and said sensor.

4. A device for measuring airway resistance comprising:
a shutter;
a flow tube having a proximal end, for engaging a patient's mouth, a distal end, for receiving said shutter to releasably occlude said flow tube, and a medial pneumatic port;
a baffle located upstream of said pneumatic port, said baffle projecting from a sidewall near said pneumatic port so as to create a negative pressure at said pneumatic port;
a sensor for measuring pressure in said flow tube during occlusion and entrainment pressure caused by air flow through the tube during exhalation, wherein said sensor is in communication with said pneumatic port; and
a shutter release mechanism to keep said flow tube closed with said shutter during occlusion and to release said shutter at the end of occlusion,
wherein said baffle has a shape dependent on flow tube geometry and the shape is further dependent on modifying an output of a combination of pressure value, pressure noise, and nonlinearity of pressure response versus flow.

5. The device as defined in claim 4 wherein a height of the baffle is selected to reach a maximum entrainment pressure as a function of flow during quiet exhalation.

6. The device as defined in claim 4 wherein a height of the baffle is selected to reduce pressure noise due to flow turbulence.

7. The device as defined in claim 4, wherein said sensor is a calorimetric thermal flow sensor having two ports, a first port being in communication with said medial pneumatic port and a second port being in communication with ambient air.

8. The device as defined in claim 4, further comprising a bacteriological filter between said medial pneumatic port and said sensor.

* * * * *